(12) United States Patent
Garcia et al.

(10) Patent No.: US 7,713,913 B2
(45) Date of Patent: May 11, 2010

(54) GLYPHOSATE COMPOSITION

(75) Inventors: Hylsa Garcia, Elizabeth, NJ (US); Dennis Nadolny, Toms River, NJ (US)

(73) Assignee: FMC Corporation, Philadelphia, PA (US)

(*) Notice: Subject to any disclaimer, the term of this patent is extended or adjusted under 35 U.S.C. 154(b) by 0 days.

(21) Appl. No.: 11/078,115

(22) Filed: Mar. 11, 2005

(65) Prior Publication Data

US 2005/0221985 A1    Oct. 6, 2005

Related U.S. Application Data

(60) Provisional application No. 60/552,556, filed on Mar. 12, 2004.

(51) Int. Cl.
*A01N 57/00* (2006.01)

(52) U.S. Cl. .................... 504/128

(58) Field of Classification Search ............... 504/128, 504/206
See application file for complete search history.

(56) References Cited

U.S. PATENT DOCUMENTS

| | | | |
|---|---|---|---|
| 5,125,958 A | 6/1992 | Poss | |
| 5,281,571 A | 1/1994 | Woodard et al. | |
| 5,489,571 A | 2/1996 | Woodard et al. | |
| 5,496,956 A | 3/1996 | Woodard et al. | |
| 5,530,126 A | 6/1996 | Woodard et al. | |
| 5,532,416 A | 7/1996 | Hamper et al. | |
| 5,536,700 A | 7/1996 | Woodard et al. | |
| 5,600,008 A | 2/1997 | Hamper et al. | |
| 5,600,016 A | 2/1997 | Hamper et al. | |
| 5,612,285 A * | 3/1997 | Arnold | 504/206 |
| 5,654,490 A | 8/1997 | Hamper et al. | |
| 5,866,723 A | 2/1999 | Hamper et al. | |
| 5,935,905 A | 8/1999 | Mito | |
| 6,117,816 A * | 9/2000 | Jimoh et al. | 504/118 |
| 6,127,318 A * | 10/2000 | Sato et al. | 504/128 |
| 6,165,939 A * | 12/2000 | Agbaje et al. | 504/105 |
| 2002/0183206 A1 | 12/2002 | Jimoh | |
| 2004/0102323 A1 | 5/2004 | Vigil | |

FOREIGN PATENT DOCUMENTS

| | | |
|---|---|---|
| WO | WO 00/78139 A2 | 12/2000 |
| WO | WO 01/70024 A2 | 9/2001 |
| WO | WO 02/063955 A2 | 8/2002 |

OTHER PUBLICATIONS

XP-002518654—"Use of preplant sulfentrazone in no-till, narrow-row, glyphosate-resistant Glycine max", Database CA [Online], Chemical Abstracts Service, Columbus, Ohio, US; Dirks, Jeremy F. et al.; retrieved from STN Database accession No. 2000:723022 "abstract" & Weed Science, 48(5), 628-639 Coden: WEESA6; ISSN: 0043-1745, 2000.

XP-002518655—"Glyphosate and carfentrazone-ethyl mixtures for the control of hard to kill weeds in zero-tillage systems in Brazil", Database CA [Online], Chemical Abstracts Service, Co umbus, Ohio, US; Foloni, L.L. et al.; retrieved fro STN Database accession No. 2004:498973 "abstract" & Congress Proceedings—BCPC International Gow, United Kingdom, Nov. 10-12, 2003, vol. 2, 1041-1046 Publisher: British Crop Protection Council, Brackell, UK. Coden: 69FNH6; ISBN: 1-901396-63-0 Congress Proc., 2003.

* cited by examiner

*Primary Examiner*—Alton N Pryor

(57) ABSTRACT

The present invention is directed to a composition comprising glyphosate and at least one taurate salt. This composition can further comprise a water-immiscible phase comprising a triazolinone herbicide and one or more aromatic solvents with an aqueous phase comprising the glyphosate and an emulsifier comprising the at least one taurate salt. The glyphosate and emulsifier of the present invention can be advantageously mixed with the triazolinone herbicide and one or more aromatic solvents to produce compositions that are chemically and physically stable.

22 Claims, No Drawings

GLYPHOSATE COMPOSITION

This application claims the benefit of U.S. Provisional Application No. 60/552,556, filed Mar. 12, 2004.

FIELD OF THE INVENTION

The present invention relates to the field of agrochemical compositions and formulations. In particular, the present invention provides a composition comprising glyphosate and at least one taurate salt. The glyphosate and at least one taurate salt of the present invention can be advantageously mixed with the triazolinone herbicide and one or more aromatic solvent to produce compositions that are chemically and physically stable. The present invention is also directed to methods of making and using such compositions.

BACKGROUND OF THE INVENTION

To enable the efficient elimination or controlling of unwanted plants in agriculture and related endeavors, it is desirable to use effective chemical herbicides on these unwanted plants. Compositions containing multiple herbicides are desirable in agricultural and related endeavors due to broadening the spectrum or range of unwanted plant species killed or controlled and varying the onset of visual symptomology.

Due to the desirability of having a composition with the above mentioned properties, the combination of a triazolinone herbicide and glyphosate salt has been disclosed in, for example, U.S. Pat. No. 5,935,905, U.S. Pat. No. 5,125,958, U.S. Pat. No. 6,127,318, PCT Publication WO 00/78139, PCT Publication WO 02/063955 and PCT Publication WO 01/70024. The combination of a triazolinone herbicide and glyphosate salt has been thought to exhibit a herbicidal effect against a very broad spectrum of unwanted plant species and a triazolinone herbicide is known to have fast onset of herbicidal activity as seen from visual symptomology, while glyphosate salt is considered to be slower with onset occurring just after typical triazolinone herbicides. This has the potential to be a very effective combination. However, a problem in the art of formulating the triazolinone herbicide and glyphosate salt mixture is in successfully achieving both chemical and physical stability in the composition over significant periods of time.

In general, a relatively small amount of the triazolinone herbicide has been used in conjunction with glyphosate. Chemical stability is most important in this type of composition to ensure the small amount of the triazolinone herbicide is fully effective. Typically, less than one percent is used commercially to keep the cost of the composition low, while still yielding spectrum and onset of visual symptomology benefits. Examples of problematic chemical degradation include hydrolysis, oxidation, dehalogenation and bond cleavage. The chemical and physical stability of a glyphosate and triazolinone herbicide composition is a key objective in the art.

SUMMARY OF THE INVENTION

The present invention provides new herbicide compositions that have superior chemical and physical stability, broad herbicidal spectrum effects and very good balance of onset of visual symptomology.

Specifically, the present invention is directed to a composition comprising glyphosate and at least one taurate salt. This composition can further comprise: (i) a water-immiscible phase comprising a triazolinone herbicide and one or more aromatic solvents with (ii) an aqueous phase comprising the glyphosate and an emulsifier comprising the at least one taurate salt. The triazolinone herbicide and glyphosate can be present, at least collectively, in a herbicidally effective amount.

The present invention is also directed to methods of making and using the compositions of the present invention.

DETAILED DESCRIPTION OF THE INVENTION

As used in this specification and unless otherwise indicated the term "herbicide" refers to a molecule or combination of molecules that retards or otherwise kills unwanted plants, such as, but not limited to, deleterious or annoying weeds, broadleaf plants, grasses, sedges, and can be used for crop protection, edifice protection, or turf protection. The term "herbicidally effective amount" means an amount necessary to produce an observable herbicidal effect on unwanted plant growth, including the effects of plant necrosis, plant death, growth inhibition, reproduction inhibition, inhibition of proliferation, and removal, destruction, or otherwise diminishing the occurrence and activity of unwanted plants.

"Glyphosate" in its strict sense is a well known acid compound defined conventionally as N-(phosphonomethyl)glycine, CAS Registry Number 1071-83-6, but the word "glyphosate" is used herein in a less restrictive sense, except where the context dictates otherwise, to encompass not only glyphosate acid but also salts (e.g. N-(phosphonomethyl)glycine salt), adducts, zwitterions and esters thereof, and compounds which are converted to glyphosate in plant tissues or which otherwise provide glyphosate ions. The term "carfentrazone" means α,2-dichloro-5-(4-(difluoromethyl)-4,5-dihydro-3-methyl-5-oxo-1H-1,2,4-triazol-1-yl)-4-fluorobenzenepropionic acid, CAS Registry Number 128621-72-7, or salts thereof. The term "carfentrazone ethyl" means ethyl α,2-dichloro-5-(4-(difluoromethyl)-4,5-dihydro-3-methyl-5-oxo-1H-1,2,4-triazol-1-yl)-4-fluorobenzenepropionate, CAS Registry Number 128639-02-1. The term "sulfentrazone" means N-(2,4-dichloro-5-(4-(difluoromethyl)-4,5-dihydro-3-methyl-5-oxo-1H-1,2,4-triazol-1-yl)phenyl)methanesulfonamide, CAS Registry Number 122836-35-5.

"Pre-emergent" is defined as application of the herbicide during the period prior to emergence of the crop plant from the ground. "Post-emergent" is defined as application of the herbicide during the period after emergence of the crop plant from the ground where the foliage of the crop plant is contacted by the herbicide. "Post-direct" is defined as application of the herbicide during the period after emergence of the crop plant from the ground where the foliage of the crop plant is not contacted by the herbicide and the herbicide application is directed to the base of the crop plant. "Pre-planting" is defined as application of the herbicide to kill existing unwanted plants prior to planting a crop plant. "Termination" is defined as application of a herbicide to kill the crop plant at an optimal harvest time and eliminate unwanted plants to assist in harvesting of the crop plant.

The term "ambient temperature" as utilized herein shall generally mean any suitable temperature found in a laboratory or other working quarter, and is generally not below about 15° C. nor above about 30° C.

As used herein, "% by weights of components in the total composition" includes the wt % of all liquid components in the composition.

The present invention relates to a composition comprising glyphosate and at least one taurate salt. This composition can further comprise a water-immiscible phase comprising a triazolinone herbicide and one or more aromatic solvents with an aqueous phase comprising the glyphosate and an emulsifier comprising at least one taurate salt. The triazolinone herbicide and glyphosate can be present, at least collectively, in a herbicidally effective amount.

Preferably, the glyphosate is at least one of a glyphosate salt or a glyphosate acid equivalent. When the triazolinone herbicide and the water immiscible phase is either present or is later to be added to the glyphosate and taurate salt solution, the glyphosate may be present in an amount of from 20% by weight to 60% by weight, more particularly 20% by weight to 55% by weight, more particularly, 30% by weight to 51% by weight, more particularly 40% by weight to 51% by weight, of all components in the total composition. These weight percentages are generally applicable both prior to and after the amount of the components in the water immiscible phase are considered.

Preferably, the triazolinone herbicide is at least one of carfentrazone-ethyl or sulfentrazone. The triazolinone herbicide may be present in an amount of from 0.1% by weight to 1.5% by weight, more particularly, 0.2% by weight to 1.2% by weight, more particularly, 0.3% by weight to 1% by weight, more particularly 0.5% by weight to 0.84% by weight, of all components in the total composition.

Preferably, the taurate salt is sodium-N-methyl-N-oleoyl taurate. When the triazolinone herbicide and water immiscible phase is either present or is later to be added to the glyphosate and taurate salt solution, the taurate salt may be present in an amount of from 1% by weight to 4% by weight, preferably, 1.5% by weight to 2.5% by weight, of all components in the total composition. These weight percentages are generally applicable both prior to and after the amount of the components in the water immiscible phase are considered. The taurate salt acts as an emulsifier when the aqueous phase containing the glyphosate is combined with the water immiscible phase containing the triazolinone herbicide.

Preferably, the emulsifier in the aqueous phase further comprises (in addition to the at least one taurate salt) at least one of an alkyl polyglycoside and an ethoxylated alcohol. The alkyl polyglycoside may be a $C_9$ to $C_{15}$ alkyl polyglycoside. The ethoxylated alcohol may be a $C_9$ to $C_{15}$ ethoxylated alcohol. Preferably, the $C_9$ to $C_{15}$ alkyl polyglycoside is a $C_9$ to $C_{11}$ alkyl D-glucopyranoside, and the $C_9$ to $C_{15}$ ethoxylated alcohol is a $C_{11}$ to $C_{14}$ ethoxylated alcohol.

When the triazolinone herbicide and water immiscible phase is present, the alkyl polyglycoside may be present in an amount of from 5% by weight to 25% by weight of all components in the total composition. When the triazolinone herbicide and water immiscible phase is present, the ethoxylated alcohol may be present in an amount of from 0.1% by weight to 1% by weight of all components in the total composition.

Preferably, the aromatic solvent in the water immiscible phase is at least one of an alkylated naphthalene aromatic or alkylated naphthalene depleted aromatic. The aromatic solvent may be present in an amount of from 1% by weight to 10% by weight, more particularly 1% by weight to 7% by weight, more particularly, 1% by weight to 5% by weight, of all components in the total composition. More particularly, the aromatic solvent may be present in an amount of 3% by weight to 7% by weight of all components in the total composition.

The composition can further comprise an anti-foam agent. When the triazolinone herbicide and water immiscible phase is present, the anti-foam agent may be present in an amount of from 0.001% by weight to 1% by weight of all components in the total composition.

A preferred embodiment of the present invention is wherein the triazolinone herbicide is carfentrazone ethyl, the glyphosate is at least one of a glyphosate salt or glyphosate acid equivalent, the emulsifier comprises sodium-N-methyl-N-oleoyl taurate, $C_9$ to $C_{11}$ alkyl D-glucopyranoside and $C_{11}$ to $C_{14}$ ethoxylated alcohol, the aromatic solvent is alkylated naphthalene aromatic. This preferred embodiment may further comprise an anti-foam agent. Preferably, the carfentrazone ethyl is present in an amount of from 0.10% by weight to 1.5% by weight, more particularly 0.2% by weight to 1.2% by weight, more particularly 0.30% by weight to 1% by weight of all components in the total composition, the glyphosate salt or glyphosate acid equivalent is present in an amount of from 20% by weight to 60% by weight, more particularly 20% by weight to 55% by weight of all components in the total composition, the sodium-N-methyl-N-oleoyl taurate is present in an amount of from 1% by weight to 4% by weight of all components in the total composition, the $C_9$ to $C_{11}$ alkyl D-glucopyranoside is present in an amount of from 5% by weight to 25% by weight of all components in the total composition and the $C_{11}$ to $C_{14}$ ethoxylated alcohol is present in an amount of from 0.1% by weight to 1% by weight of all components in the total composition, the alkylated naphthalene aromatic is present in an amount of from 1% by weight to 10% by weight of all components in the total composition and may further comprise an anti-foam agent present in an amount of from 0.001% by weight to 1% by weight of all components in the total composition. Even more preferably, the carfentrazone ethyl is present in an amount of from 0.2% by weight to 1.2% by weight, more particularly, 0.30% by weight to 1% by weight, more particularly, 0.5% by weight to 0.84% by weight of all components in the total composition, the glyphosate salt or glyphosate acid equivalent is present in an amount of from 30% by weight to 51% by weight, more particularly 40% by weight to 51% by weight of all components in the total composition, the sodium-N-methyl-N-oleoyl taurate is present in an amount of from 1.5% by weight to 2.5% by weight of all components in the total composition, the $C_9$ to $C_{11}$ alkyl D-glucopyranoside is present in an amount of from 9% by weight to 11% by weight of all components in the total composition, the $C_{11}$ to $C_{14}$ ethoxylated alcohol is present in an amount of from 0.2% by weight to 0.6% by weight of all components in the total composition, the alkylated naphthalene aromatic is present in an amount of from 1% by weight to 7% by weight, more particularly 1% by weight to 5% by weight, even more particularly 3% by weight to 7% by weight of all components in the total composition, and may further comprise an anti-foam agent present in an amount of from 0.005% by weight to 0.8% by weight, more particularly 0.005% by weight to 0.1% by weight of all components in the total composition.

Another embodiment of the present invention is a method for the control of unwanted plants comprising applying a herbicidally effective amount of the composition of the invention to an area where such control is desired. Such unwanted plants include broadleaf plants, grasses and sedges. The application to unwanted plants is pre-planting, pre-emergent, post-emergent, post-directed or at termination of or to a crop plant. The crop plant includes wheat, corn, rice, soybeans, barley, oats, small grains, cotton, sugarcane, oil seed crops, forage crops, tree crops, vine crops, industrial vegetation control, forestry, vegetable crops or fruiting vegetables crops.

Yet another embodiment of the present invention is a process for preparing the composition comprising combining the glyphosate and at least one taurate salt in any conventional manner. A process for preparing the composition containing the glyphosate and triazolinone herbicide of the invention comprises: a) preparing a water immiscible phase by combining the triazolinone herbicide with one or more aromatic solvents and heating, b) preparing an aqueous phase by combining the glyphosate, emulsifier and water, and mixing until dispersed, and c) combining the mixture of step a) with the mixture of step b) and emulsifying. Steps a) and b) may be performed in any order. More preferably, wherein the heating of step a) may be at 50° C.-70° C., the mixing of step b) is at 600 revolutions per minute, the combining the mixture of step c) is under agitation at 600 revolutions per minute, and the emulsifying the mixture in step c) may be at 1,200 to 1,500 revolutions per minute, more particularly 1,200 revolutions per minute at ambient temperature and for a period of one to five minutes.

The compositions of the present invention are further illustrated by the examples below. Unless otherwise specified in the examples, the carfentrazone-ethyl used in the Examples below contained 91.2% active ingredient and the glyphosate used contained 62% active ingredient. The examples serve only to illustrate the invention and should not be interpreted as limiting since further modifications of the disclosed invention will be apparent to those skilled in the art. All such modifications are deemed to be within the scope of the invention as defined in the claims.

Example 1

This example illustrates one protocol for the preparation of a 480 grams/liter glyphosate salt composition of the present invention (Composition A).

A mixture of 4.4 grams of carfentrazone-ethyl and 20 grams of alkylated naphthalene depleted aromatic solvent (Aromatic 200 ND) was heated to about 70° C. In a separate vessel, 86.75 grams of water was heated to about 55° C. Upon reaching temperature, 1.85 grams of sodium chloride, 10.0 grams of sodium-N-methyl-N-oleoyl taurate (Geropon T77 available from Rhodia), 325.0 grams of glyphosate, 50.0 grams of $C_9$ to $C_{11}$ alkyl D-glucopyranoside (Agnique PG 9116 available from Cognis), and 2.0 grams of $C_{11}$-$C_{14}$ ethoxylated alcohol (Renex 36 available from Uniqema) were added to the heated water. The aqueous solution was mixed with a Lightning mixer at about 600 revolutions per minute for 15 minutes. The carfentrazone-ethyl in solvent was then added slowly to the aqueous solution as it was agitated. Upon completion of the addition, the agitation was increased to 1,200 revolutions per minute for 5 minutes. The resultant emulsion particle size was 1.9 microns and the batch was complete.

Example 2

This example illustrates one protocol for the preparation of a 600 grams/liter glyphosate salt composition of the present invention (Composition B).

A mixture of 3.78 grams of carfentrazone-ethyl and 8.58 grams of alkylated naphthalene depleted aromatic solvent (Aromatic 200 ND) was heated to about 70° C. In a separate vessel, 29.83 grams of water, 1.59 grams of sodium chloride and 8.58 grams of sodium-N-methyl-N-oleoyl taurate (Geropon T77 available from Rhodia) were mixed using a Lightning mixer at 1,800 revolutions per minute at ambient temperature. Upon dissolving the Geropon T77 into the water, 332.19 grams of glyphosate, 42.92 grams of $C_9$ to $C_{11}$ alkyl D-glucopyranoside (Agnique PG 9116 available from Cognis), and 1.72 grams of $C_{11}$-$C_{14}$ ethoxylated alcohol (Renex 36 available from Uniqema) were added to the aqueous solution and mixed with a Lightning mixer at 1,200 revolutions per minute at ambient temperature. The carfentrazone-ethyl in solvent was then added slowly to the aqueous solution as it was agitated. Upon completion of the addition, the agitation was maintained for 5 minutes at ambient temperature. The resultant emulsion particle size was 1.6 microns and the batch was complete.

Example 3

This example illustrates one protocol for the preparation of a 600 grams/liter glyphosate salt composition of the present invention (Composition C).

A mixture of 2.75 grams of carfentrazone-ethyl and 10.0 grams of alkylated naphthalene depleted aromatic solvent (Aromatic 200 ND) was heated to about 70° C. In a separate vessel, 19.85 grams of water, 1.85 grams of sodium chloride and 10.0 grams of sodium-N-methyl-N-oleoyl taurate (Geropon T77 available from Rhodia) were mixed using a Lightning mixer at 600 revolutions per minute at ambient temperature. Upon dissolving the Geropon T77 into the water, 403.5 grams of glyphosate, 50.0 grams of $C_9$ to $C_{11}$ alkyl D-glucopyranoside (Agnique PG 9116 available from Cognis), and 2.0 grams of $C_{11}$-$C_{14}$ ethoxylated alcohol (Renex 36 available from Uniqema) were added to the aqueous solution and mixed with a Lightning mixer at 600 revolutions per minute at ambient temperature. Agitation was increased to 1,200 revolutions per minute, and the carfentrazone-ethyl in solvent was then added slowly to the aqueous solution as it was agitated. Upon completion of the addition, the agitation was maintained for 5 minutes at ambient temperature. Due to foaming, 0.05 grams of Dow Antifoam was added to the emulsion. The resultant emulsion particle size was 0.8 microns and the batch was complete.

Example 4

This example illustrates one protocol for the preparation of a 600 grams/liter glyphosate salt composition of the present invention (Composition D).

A mixture of 4.57 grams of carfentrazone-ethyl and 10.0 grams of alkylated naphthalene depleted aromatic solvent (Aromatic 200 ND) was heated to about 70° C. In a separate vessel, 18.33 grams of water, 1.85 grams of sodium chloride and 10.0 grams of sodium-N-methyl-N-oleoyl taurate (Geropon T77 available from Rhodia) were mixed using a Lightning mixer at 600 revolutions per minute at ambient temperature. Upon dissolving the Geropon T77 into the water, 403.25 grams of glyphosate, 50.0 grams of $C_9$ to $C_{11}$ alkyl D-glucopyranoside (Agnique PG 9116 available from Cognis), and 2.0 grams of $C_{11}$-$C_{14}$ ethoxylated alcohol (Renex 36 available from Uniqema) were added to the aqueous solution. Agitation at 600 revolutions per minute at ambient temperature continued until the aqueous solution was well mixed. Agitation was then increased to 1,200 revolutions per minute and the carfentrazone-ethyl in solvent was added slowly to the aqueous solution. Upon completion of the addition, the agitation was maintained for 2 minutes at ambient temperature. The resultant emulsion particle size was 2.6 microns and the batch was complete.

Example 5

This example illustrates one protocol for the preparation of a 600 grams/liter glyphosate salt composition of the present invention (Composition E).

A mixture of 2.75 grams of carfentrazone-ethyl and 10.0 grams of alkylated naphthalene depleted aromatic solvent (Aromatic 200 ND) was heated to about 70° C. In a separate vessel, 4.85 grams of water, 1.85 grams of sodium chloride and 35.0 grams of sodium-N-methyl-N-oleoyl taurate (Geropon T22 available from Rhodia) were mixed using a Lightning mixer at 600 revolutions per minute at ambient temperature. Upon dissolving the Geropon T22 into the water, 403.5 grams of glyphosate, 40.0 grams of $C_9$ to $C_{11}$ alkyl D-glucopyranoside (Agnique PG 9116 available from Cognis), and 2.0 grams of $C_{11}$-$C_{14}$ ethoxylated alcohol (Renex 36 available from Uniqema) were added to the aqueous solution. Agitation at 600 revolutions per minute at ambient temperature continued until the aqueous solution was well mixed. Agitation was then increased to 1,000 revolutions per minute and the carfentrazone-ethyl in solvent was added slowly to the aqueous solution. Upon completion of the addition, the agitation was maintained for 5 minutes at ambient temperature. Due to foaming, 0.05 grams of Dow Antifoam was added to the emulsion. The resultant emulsion particle size was 1.7 microns and the batch was complete.

Example 6

This example illustrates one protocol for the preparation of a 600 grams/liter glyphosate salt composition of the present invention (Composition F).

A mixture of 2.75 grams of carfentrazone-ethyl and 10.0 grams of alkylated naphthalene aromatic solvent (Aromatic 200) was heated to about 70° C. In a separate vessel, 4.65 grams of water, 1.85 grams of sodium chloride and 35.0 grams of sodium-N-methyl-N-oleoyl taurate (Geropon T22 available from Rhodia) were mixed using a Lightning mixer at 600 revolutions per minute at ambient temperature. Upon dissolving the Geropon T22 into the water, 403.5 grams of glyphosate, 40.0 grams of $C_9$ to $C_{11}$ alkyl D-glucopyranoside (Agnique PG 9116 available from Cognis), and 2.0 grams of $C_{11}$-$C_{14}$ ethoxylated alcohol (Renex 36 available from Uniqema) were added to the aqueous solution. Agitation at 600 revolutions per minute at ambient temperature continued until the aqueous solution was well mixed. Agitation was then increased to 1,200 revolutions per minute and the carfentrazone-ethyl in solvent was added slowly to the aqueous solution. Upon completion of the addition, the agitation was maintained for 5 minutes at ambient temperature. Due to foaming, 0.25 grams of Dow Antifoam was added to the emulsion. The resultant emulsion particle size was 2 microns and the batch was complete.

Example 7

This example illustrates one protocol for the preparation of a 360 grams/liter glyphosate acid equivalent composition of the present invention (Composition G).

A mixture of 0.94 grams of carfentrazone-ethyl (92% AI) and 10.02 grams of alkylated naphthalene aromatic solvent (Aromatic 200) was heated to about 70° C. In a separate vessel, 28.44 grams of water and 4.0 grams of sodium-N-methyl-N-oleoyl taurate (Geropon T77 available from Rhodia) were heated to about 70° C. Upon dissolving the Geropon T77 into the water, 134.8 grams of glyphosate (46% acid equivalent), 20.0 grams of $C_9$ to $C_{11}$ alkyl D-glucopyranoside (Agnique PG 9116 available from Cognis), 0.80 grams of $C_{11}$-$C_{14}$ ethoxylated alcohol (Renex 36 available from Uniqema) and 1.00 gram of Dow Antifoam were added to the aqueous solution. The aqueous solution was heated an additional 10 minutes at about 70° C. The carfentrazone-ethyl in solvent was then added slowly to the aqueous solution and agitated using an impeller type mixer at 1,500 revolutions per minute for 30 minutes. The resultant emulsion particle size was 0.51 microns and the batch was complete.

Example 8

This example illustrates one protocol for the preparation of a 360 grams/liter glyphosate acid equivalent composition of the present invention (Composition H).

A mixture of 0.58 grams of carfentrazone-ethyl (92% AI) and 10.38 grams of alkylated naphthalene aromatic solvent (Aromatic 200) was heated to about 70° C. In a separate vessel, 29.44 grams of water, 4.0 grams of sodium-N-methyl-N-oleoyl taurate (Geropon T77 available from Rhodia) and 133.8 grams of glyphosate (46% acid equivalent) were heated to about 70° C. Upon dissolving the Geropon T77 and glyphosate into the water, 20.0 grams of $C_9$ to $C_{11}$ alkyl D-glucopyranoside (Agnique PG 9116 available from Cognis), 0.80 grams of $C_{11}$-$C_{14}$ ethoxylated alcohol (Renex 36 available from Uniqema) and 1.00 gram of Dow Antifoam were added to the aqueous solution. The aqueous solution was heated an additional 10 minutes at about 70° C. The carfentrazone-ethyl in solvent was then added slowly to the aqueous solution and agitated using an impeller type mixer at 1,500 revolutions per minute for 30 minutes. The resultant emulsion particle size was 0.5 microns and the batch was complete.

Example 9

This example illustrates one protocol for the preparation of a 600 grams/liter glyphosate salt composition of the present invention (Composition I).

A mixture of 2.2 grams of carfentrazone-ethyl (92% AI) and 8.0 grams of alkylated naphthalene aromatic solvent (Aromatic 200) was heated to about 70° C. In a separate vessel, 2.3 grams of water, 4.4 grams of sodium-N-methyl-N-oleoyl taurate (Geropon T77 available from Rhodia) and 161.3 grams of glyphosate were mixed using a Lightning mixer at 600 revolutions per minute at ambient temperature. Upon complete mixing of the Geropon T77 with the water and glyphosate, 20.0 grams of $C_9$ to $C_{11}$ alkyl D-glucopyranoside (Agnique PG 9116 available from Cognis) and 0.8 grams of $C_{11}$-$C_{14}$ ethoxylated alcohol (Renex 36 available from Uniqema) were added to the aqueous solution and mixed with a Lightning mixer at 600 revolutions per minute at ambient temperature. Agitation was increased to 1,500 revolutions per minute, and the carfentrazone-ethyl in solvent was then added slowly to the aqueous solution as it was agitated. Upon completion of the addition, the agitation was maintained for 1 minute at ambient temperature. Due to foaming, 1.0 gram of Dow Antifoam was added to the emulsion. The resultant emulsion particle size was 2.0 microns and the batch was complete.

Example 10

Stability Studies

This example sets forth stability studies that were accomplished on compositions prepared in accordance with the present invention.

Laboratory tests that show the stability of the emulsion compositions were carried out in the following manner. Prior to commencing the stability tests, an initial percentage of carfentrazone-ethyl present in Compositions A, B, C, G, H and I prepared above was determined by chromatographic techniques. After this determination, the compositions were stored at 50° C. for a period of one month to model extreme conditions. After this time, the percentage of active ingredient present in the composition was determined by the same chromatographic technique. The results of these tests are presented in Table 1 below.

TABLE 1

|  | Original GC weight % | One Month at 50° C. GC weight % |
|---|---|---|
| Composition A | 0.84 | 0.82 |
| Composition B | 0.83 | 0.78 |
| Composition C | 0.50 | 0.46 |
| Composition G | 0.44 | 0.42 |
| Composition H | 0.28 | 0.26 |
| Composition I | 0.95 | 0.94 |

The results, shown in Table 1, indicate that the compositions of the present invention maintained chemical stability at elevated temperature.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A composition comprising:
   a) a water immiscible phase comprising:
      i) at least one triazolinone herbicide selected from the group consisting of carfentrazone ethyl and sulfentrazone, and
      ii) one or more aromatic solvents selected from the group consisting of an alkylated naphthalene aromatic and an alkylated naphthalene depleted aromatic; and
   b) an aqueous phase comprising:
      i) glyphosate, and
      ii) an emulsifier comprising at least one taurate salt;
   wherein said at least one taurate salt is present in an amount of from 1.5% to 2.5% by weight of all components in the total composition; said taurate salt is sodium-N-methyl-N-oleoyl taurate; said triazolinone herbicide and glyphosate are present, at least collectively, in a herbicidally effective amount; and said emulsifier further comprises a $C_9$ to $C_{15}$ alkyl polyglycoside and a $C_9$ to $C_{15}$ ethoxylated alcohol.

2. The composition of claim 1, wherein:
   a) said $C_9$ to $C_{15}$ alkyl polyglycoside is a $C_9$ to $C_{11}$ alkyl D-glucopyranoside; and
   b) said $C_9$ to $C_{15}$ ethoxylated alcohol is a $C_{11}$ to $C_{14}$ ethoxylated alcohol.

3. The composition of claim 1, wherein said $C_9$ to $C_{15}$ alkyl polyglycoside is present in an amount of from 5% by weight to 25% by weight of all components in the total composition.

4. The composition of claim 1, wherein said $C_9$ to $C_{15}$ ethoxylated alcohol is present in an amount of from 0.1% by weight to 1% by weight of all components in the total composition.

5. The composition of claim 1, wherein said glyphosate is at least one of a glyphosate salt or a glyphosate acid equivalent.

6. The composition of claim 1, wherein said glyphosate is present in an amount of from 20% by weight to 60% by weight of all components in the total composition.

7. The composition of claim 1, wherein said triazolinone herbicide is present in an amount of from 0.1% by weight to 1.5% by weight of all components in the total composition.

8. The composition of claim 1, wherein said aromatic solvent is present in an amount of from 1% by weight to boo by weight of all components in the total composition.

9. The composition of claim 1, further comprising an anti-foam agent.

10. The composition of claim 9, wherein said anti-foam agent is present in an amount of from 0.001% by weight to 1% by weight of all components in the total composition.

11. The composition of claim 1, wherein:
   a) said triazolinone herbicide is carfentrazone ethyl;
   b) said glyphosate is at least one of a glyphosate salt or a glyphosate acid equivalent;
   c) said $C_9$ to $C_{15}$ alkyl polyglycoside comprises a $C_9$ to $C_{11}$ alkyl D-glucopyranoside and said $C_9$ to $C_{15}$ ethoxylated alcohol comprises a $C_{11}$ to $C_{14}$ ethoxylated alcohol; and
   d) said aromatic solvent is said alkylated naphthalene aromatic.

12. The composition of claim 11, wherein:
   a) said carfentrazone ethyl is present in an amount of from 0.10% by weight to 1.5% by weight of all components in the total composition;
   b) said glyphosate salt or glyphosate acid equivalent is present in an amount of from 20% by weight to 60% by weight of all components in the total composition;
   c) said $C_9$ to $C_{11}$ alkyl D-glucopyranoside is present in an amount of from 5% by weight to 25% by weight of all components in the total composition and said $C_{11}$ to $C_{14}$ ethoxylated alcohol is present in an amount of from 0.1% by weight to 1% by weight of all components in the total composition; and
   d) said alkylated naphthalene aromatic is present in an amount of from 1% by weight to 10% by weight of all components in the total composition.

13. The composition of claim 11, wherein:
   a) said carfentrazone ethyl is present in an amount of from 0.2% by weight to 1.2% by weight of all components in the total composition;
   b) said glyphosate salt or glyphosate acid equivalent is present in an amount of from 30% by weight to 51% by weight of all components in the total composition;
   c) said $C_9$ to $C_{11}$ alkyl D-glucopyranoside is present in an amount of from 9% by weight to 11% by weight of all components in the total composition and said $C_{11}$ to $C_{14}$ ethoxylated alcohol is present in an amount of from 0.2% by weight to 0.6% by weight of all components in the total composition; and
   d) said alkylated naphthalene aromatic is present in an amount of from 3% by weight to 7% by weight of all components in the total composition.

14. The composition of claim 11, wherein the composition further comprises an anti-foam agent.

15. The composition of claim 12, wherein the composition further comprises an anti-foam agent present in an amount of from 0.001% by weight to 1% by weight of all components in the total composition.

16. The composition of claim 13, wherein the composition further comprises an anti-foam agent present in an amount of from 0.005% by weight to 0.8% by weight of all components in the total composition.

17. A method for controlling unwanted plants comprising applying a herbicidally effective amount of the composition of claim 1 to an area where said controlling is desired.

18. The method of claim 17, wherein said unwanted plants are selected from the group consisting of broadleaf plants, grasses and sedges.

19. The method of claim 17, wherein applying to unwanted plants is pre-planting, pre-emergent, post-emergent, post-directed or at termination of a crop plant.

20. The method of claim 19, wherein said crop plant is wheat, corn, rice, soybeans, barley, oats, small grains, cotton, sugarcane, oil seed crops, forage crops, tree crops, vine crops, industrial vegetation control, forestry, vegetable crops or fruiting vegetables crops.

21. A process for preparing a composition of claim 1 comprising:
   a) combining the triazolinone herbicide with one or more aromatic solvents and heating;
   b) combining the glyphosate, emulsifier and water, and mixing until dispersed; and
   c) combining the mixture of step a) with the mixture of step b) and emulsifying.

22. The process of claim 21, wherein:
   a) said heating of step a) is from 50° C.-70° C.;
   b) said mixing of step b) is at 600 revolutions per minute;
   c) combining the mixture in step c) under agitation at 600 revolutions per minute; and
   d) emulsifying the mixture in step c) at 1,200 to 1,500 revolutions per minute, at ambient temperature and for a period of one to five minutes.

* * * * *

UNITED STATES PATENT AND TRADEMARK OFFICE
CERTIFICATE OF CORRECTION

PATENT NO.        : 7,713,913 B2                                             Page 1 of 1
APPLICATION NO.   : 11/078115
DATED             : May 11, 2010
INVENTOR(S)       : Hylsa Garcia et al.

It is certified that error appears in the above-identified patent and that said Letters Patent is hereby corrected as shown below:

Column 10, line 5, change "boo" to --10%--

Signed and Sealed this

Sixteenth Day of November, 2010

David J. Kappos
*Director of the United States Patent and Trademark Office*